United States Patent [19]

Ploumen et al.

[11] Patent Number: 6,093,336
[45] Date of Patent: Jul. 25, 2000

[54] PROCESS FOR MAKING SOLID COMPOSITIONS COMPRISING QUATERNARY ESTER AMMONIUM COMPOUNDS AND FATTY ACIDS

[75] Inventors: Jan Joseph Hubert Ploumen, WC Roermond; Kornelis Overkempe, WH Holten; Paulus Gerhardus Johannes Nieuwenhuis, PH Okkenbroek, all of Netherlands

[73] Assignee: Akzo Nobel nv, Arnhem, Netherlands

[21] Appl. No.: 09/198,183

[22] Filed: Nov. 23, 1998

Related U.S. Application Data

[63] Continuation of application No. PCT/EP97/02960, May 30, 1997.

[30] Foreign Application Priority Data

May 31, 1996 [EP] European Pat. Off. .............. 96201524

[51] Int. Cl.$^7$ .......................... D06M 13/463; C11D 1/62; C11D 11/00
[52] U.S. Cl. ......................... 252/8.63; 510/446; 510/451; 510/504; 510/515
[58] Field of Search .............................. 516/67; 510/504, 510/446, 451, 515; 252/8.63

[56] References Cited

U.S. PATENT DOCUMENTS

| Re. 34,062 | 9/1992 | Wells | 252/8.63 X |
|---|---|---|---|
| 4,184,970 | 1/1980 | Draper, Jr. | 510/504 X |
| 4,840,738 | 6/1989 | Hardy et al. | 252/8.6 |
| 5,223,628 | 6/1993 | Whittlinger | 510/515 X |
| 5,427,696 | 6/1995 | Phan et al. | 252/8.63 X |
| 5,480,567 | 1/1996 | Lam et al. | 252/8.8 |
| 5,516,438 | 5/1996 | Turner | 510/515 |
| 5,747,108 | 5/1998 | Farooq et al. | 510/504 X |

FOREIGN PATENT DOCUMENTS

| 0 440 229 | 8/1991 | European Pat. Off. | C07C 211/63 |
|---|---|---|---|
| 0 445 525 | 9/1991 | European Pat. Off. | C07C 209/00 |
| 0 704 522 | 4/1996 | European Pat. Off. | C11D 1/835 |
| 58-11033 | 1/1983 | Japan | B01J 2/30 |
| WO 92/18593 | 10/1992 | WIPO | C11D 1/835 |
| WO 94/21593 | 9/1994 | WIPO | C07C 213/06 |
| WO 95/14654 | 6/1995 | WIPO | C07C 217/50 |

OTHER PUBLICATIONS

Ullman's Encyclopedia of Industrial Chemistry, 5$^{th}$ ed., vol. B3, *Evaporation*, pp. 3–14 (1988).
*International Search Report*, dated Oct. 23, 1997.

*Primary Examiner*—Richard D. Lovering
*Attorney, Agent, or Firm*—Ralph J. Mancini; Lainie E. Parker

[57] ABSTRACT

A process is disclosed for making a solid composition comprising at least one quaternary ester ammonium compound and at least one substantially saturated fatty acid compound, a solid composition obtainable by that process, and a solid composition containing essentially more than 50 wt % of at least one quaternary ester ammonium compound, at most 50 wt % of at least one substantially saturated fatty acid compound, and less than 5.5 wt % of impurities.

19 Claims, No Drawings

PROCESS FOR MAKING SOLID COMPOSITIONS COMPRISING QUATERNARY ESTER AMMONIUM COMPOUNDS AND FATTY ACIDS

This is a continuation of PCT International application No. PCT/EP97/02960 filed on May 30, 1997.

FIELD OF THE INVENTION

The present invention generally relates to a process for preparing a solid composition comprising a quaternary ester ammonium compound and a fatty acid compound and to a solid composition obtainable by said process.

BACKGROUND OF THE INVENTION

Quaternary ester ammonium compounds are rapidly biodegradable compounds which may therefore be used in various applications. However, they are also more subject to hydrolysis than are conventional quaternary ammonium compounds, e.g., ditallow dimethyl ammonium chloride. More particularly, during the preparation process of the quaternary ester ammonium compounds hydrolysis of the compounds may occur in the presence of water at high temperatures. These kind of side reactions have to be prevented, as they result in high amounts of impurities which reduce the hardness of the final composition.

Also, some of these quaternary ester ammonium compounds are hygroscopic, i.e., they have the ability to take up water. This results in caking of the compositions during storage and hydrolysis of the compounds. Although the storage temperature will be lower than the process preparation temperature, the period of time in storage is of course longer and, accordingly, hydrolysis cannot be prevented in the long term. A decrease in storage stability is the result.

With any solution to the above-mentioned problems, it has to be kept in mind that in all applications wherein quaternary ester ammonium compounds can be employed, it is preferred that the compound is added as pure as possible. Accordingly, if a second compound is necessary to prevent the above-mentioned disadvantages it should be present in the composition in an amount as low as possible. More particularly, the composition should comprise the quaternary ester ammonium compound in an amount as high as possible, i.e., the composition should have a high content of active matter.

In view of the above, it is one of the objects of the present invention to provide a process to prepare compositions comprising quaternary ester ammonium compounds with a very small amount of impurities. Also, it is an object to provide storage stable and non-caking compositions. Finally, it is an object to provide compositions comprising a high amount of quaternary ester ammonium compounds.

Various processes are known to prepare solid compositions comprising a quaternary ammonium compound and a fatty acid compound. WO 92/18593 discloses the preparation of a composition comprising a quaternary ester ammonium compound and a fatty acid compound in two ways. A first process comprises the steps of mixing the two compounds together by melting the fatty acid compound and subsequently mixing the quaternary ester ammonium compound in the molten fatty acid compound. A second process shows the quaternization of an ester amine compound in a molten fatty acid compound. Both processes have the disadvantage that the resulting compositions comprise a high amount of impurities which affect the properties of the compositions. Furthermore, the resulting solid compositions comprise the quaternary ester ammonium compound in an amount of 50 wt % or lower, preferably 5 to 30 wt %. Exemplified are compositions comprising at most 25 wt % of quaternary ester ammonium compound.

U.S. Pat. No. 4,840,738 discloses solid compositions comprising quaternary ester ammonium compounds and a second compound. This second compound is selected from potassium sulfate, micronized silica, and powdered urea. Fatty acid compounds are not mentioned. Furthermore, the quaternary ester ammonium compound is present in an amount up to 20 wt % in the composition. Finally, the disclosed preparation process comprises mixing the quaternary ester ammonium compound with the second compound. The latter is not added during the quaternization process.

JP-A-58011033 discloses agents to prevent solidification of inorganic salts. Among a list of agents quaternary ester ammonium compounds are mentioned, such as choline bitartrate, choline dihydrogen citrate, and choline gluconate. Optionally, the agents may be mixed with, among others, alkali salts of higher fatty acid compounds. However, mixtures of a quaternary ester ammonium compound and a fatty acid compound are not disclosed. Neither is mentioned in which quantities the compounds should be mixed. Finally, the object to achieve in the Japanese publication is to use the hygroscopic property of the agents to prevent solidification of the inorganic salts. This is the direct opposite from the object of the present invention to reduce the hygroscopic effect of the quaternary ester ammonium compound.

From EP-A-0445525 it is known to prepare a quaternary ether ammonium compound by carrying out the quaternization reaction in the presence of a relatively small amount of a water-alcohol solvent after which a fatty acid compound is added and the solvent is removed. Process temperatures range from 50–120° C. Quaternary ester ammonium compounds are not disclosed.

Finally, EP-A-0704522 describes a dryer-activated fabric softening composition comprising quaternary ester ammonium compound and an unsaturated fatty acid having an iodine value (IV) of 3 to 60, preferably of 12 to 45. The unsaturated fatty acid is added to improve the processability of the composition, i.e., to reduce the viscosity and ease the handling, and improve the antistatic performance of the composition. Saturated fatty acids harm softening and/or antistatic performance. Examples are given of unsaturated fatty acids having iodine values of 40–50. This publication also relates to a process for preparing such compositions and to a process for preparing the quaternary ester ammonium compound. In this latter process, an unsaturated fatty acid having an IV of 3–60, preferably 8 to 50, is added during the quaternization in order to reduce and/or maintain the viscosity of the reaction mixture.

Furthermore, it has been established that the preparation of quaternary ester ammonium compounds cannot be carried out in the presence of water at these temperatures in view of the above-mentioned disadvantages.

SUMMARY OF THE INVENTION

The present invention relates to a process for preparing a solid composition comprising at least one quaternary ester ammonium compound and at least one substantially saturated fatty acid compound, a solid composition obtainable by that process, and a solid composition containing essentially more than 50 wt % of at least one quaternary ester ammonium compound, at most 50 wt % of at least one substantially saturated fatty acid compound, and less than 5.5 wt % of impurities.

DETAILED DESCRIPTION OF THE INVENTION

The process of the present invention comprises the steps of:

quaternizing a tertiary ester amine with a quaternizing agent in a substantially water-free solvent to obtain a quaternary ester ammonium compound, adding a substantially saturated fatty acid to the reaction mixture comprising the quaternary ester ammonium compound, removing the solvent, and solidifying the resulting mixture.

The present process has the advantages of preparing a storage stable and non-caking composition comprising at least one quaternary ester ammonium compound, at least one substantially saturated fatty acid compound, and a very low amount of impurities.

Preferably, quaternary ester ammonium compounds prepared by the process of the present invention are selected from the following formulae I or II:

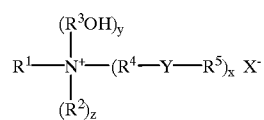
(I)

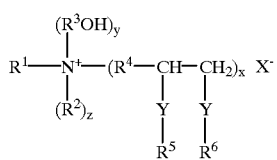
(II)

wherein $X^-$ is an anion;

Y is —O—C(O)—, —C(O)—O—, or —O—C(O)—O—;

x, y, and z are independently chosen from a range from 0 to 3, whereby x+y+z=3, and x is not 0;

$R^1$ is a linear or branched $C_{1-30}$ alkyl group, optionally comprising one or more unsaturated bonds;

$R^2$ is a linear or branched $C_{1-4}$ alkyl group, optionally substituted with one or more hydroxyl groups or a phenyl group;

$R^1$ and $R^2$ may be linked together to form a ring with the central quaternary nitrogen atom, optionally via a heteroatom selected from the group of nitrogen, oxygen, and sulfur;

$R^3$ is a linear or branched $C_{1-30}$ alkylene group, optionally comprising one or more unsaturated bonds;

$R^4$ is a linear or branched $C_{1-4}$ alkylene group, optionally comprising one or more unsaturated bonds, optionally substituted with one or more hydroxyl groups; and $R^5$ and $R^6$ are independently a linear or branched $C_{1-30}$ alkyl group, optionally comprising one or more unsaturated bonds, ester, or ether groups.

$X^-$ is preferably selected from the group of chloride, bromide, iodide, fluoride, sulfate, methyl sulfate, nitrate, formate, phosphate, dimethyl phosphonate, carbonate, borate, acetate, propionate, citrate, adipate, and benzoate.

Preferably, Y is —O—C(O)—.

Preferably, the quaternary ester ammonium compound is selected from compounds having formula 1. More preferably, the quaternary ester ammonium compounds have one of the following configurations:

$R^1$ and $R^2$ are methyl groups and x=1, y=0, and z=2;

$R^1$ is a methyl group and x=1, y=2, and z=0; or $R^1$ and $R^2$ are methyl groups and x=1, y=1, and z=1.

Preferably, $R^3$ is an ethylene group.

It also preferred that $R^4$ is an ethylene group.

Finally, it is preferred that $R^5$ is a $C_{6-30}$ alkyl group, more preferably selected from the group of heptyl, nonyl, undecyl, tridecyl, pentadecyl, heptadecyl, heptadecenyl, heptadecadienyl, nonadecyl, henicosyl, and mixtures thereof. Most preferably, $R^5$ is heptyl, nonyl, undecyl, tridecyl, or mixtures thereof, i.e., the group Y—$R^5$ being derived from cocoyl fatty acid. It is even more preferred that the quaternary ester ammonium compounds are water-soluble.

Examples of quaternary ester ammonium compounds include:

cocoyl ester of 2-hydroxyethyl trimethyl ammonium salts;

cocoyl ester of bis(2-hydroxyethyl) dimethyl ammonium salts;

cocoyl ester of tris(2-hydroxyethyl) methyl ammonium salts;

cocoyl ester of 2-hydroxyethyl dimethyl benzyl ammonium salts;

cocoyl ester of 2-hydroxyethyl (2-ethoxy-2-oxoethyl) dimethyl ammonium salts; and octanoyl ester of 2-hydroxyethyl trimethyl ammonium salts.

In particular, chlorides are preferred.

Suitable examples of quaternary ester ammonium compounds having formula II include hydrogenated tallow and cocoyl diesters of 3-trimethylammonium-1,2-propanediol salts, in particular, the chlorides.

Preferably, the tertiary ester amine to be used in the process of the present invention to prepare the quaternary ester ammonium compounds is selected from the following formulae III and IV:

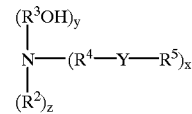
(III)

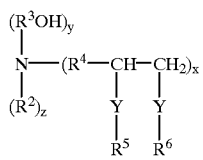
(IV)

Y, $R^2$, $R^3$, $R^4$, $R^5$, $R^6$, x, y, and z are as mentioned above.

Preferably, the quaternizing agent has the formula $(R^1)_n$—X wherein X is selected from the group of chloride, bromide, iodide, fluoride, sulfate, ethyl sulfate, nitrate, formate, phosphate, trimethyl phosphite, carbonate, borate, acetate, propionate, citrate, adipate, and benzoate, n is an integer selected from 1 or 2, and $R^1$ is as mentioned above. Examples include dimethyl sulfate, diethyl sulfate, methyl chloride, methyl bromide, methyl iodide, benzyl chloride, benzyl bromide, allyl chloride, and allyl bromide.

The solvent is preferably a polar volatile solvent. More preferably, it is selected from the group of $C_{1-5}$ alkanols, such as methanol, ethanol, propanol, butanol, and pentanol, and their isomers, such as isopropanol, isobutanol, t-butanol, and combinations thereof. Isopropanol is most preferred. The solvent is substantially water-free, i.e., contains less than 4 wt %, preferably less than 1 wt %, more preferably less than 0.5 wt %, based upon a reaction mixture comprising the tertiary ester amine, quaternizing agent, and solvent. Most preferably, water is excluded from the reaction.

Preferably, the substantially saturated fatty acid is a linear or branched $C_{6-30}$ fatty acid, more preferably a $C_{12-22}$ fatty acid, most preferably the fatty acid is lauric, myristic, palmitic, stearic, or cocoyl fatty acid. With substantially saturated fatty acid is meant a fatty acid having an iodine value (IV) of from 0 to less than 3. Preferably, the fatty acid has an IV of from 0 to 1, more preferably of from 0 to 0.5.

In the process of the present invention, the tertiary ester amine and the solvent are added to the reactor and heated up to a temperature of maximum 150° C. Preferably, the reaction is carried out in an inert atmosphere, preferably nitrogen. The quaternizing agent is added incrementally so as to maintain a reaction temperature up to 150° C., preferably from about 50 to about 100° C. and especially from about 60 to about 90° C. It is standard practice in the art to add the quaternizing agent incrementally since the quaternization reaction is generally exothermic and the temperature of the reaction can be controlled by this type of addition, optionally in combination with a cooling device. The quaternization is preferably carried out under pressure, e.g., 2 to $2 \times 10^6$ Pa, more preferably $2 \times 10^5$ to $10^6$ Pa.

The progress of the reaction is followed by measuring the amount of free tertiary amine in the reaction mixture. When that amount has stabilized, preferably in an amount less than 3% by weight, the quaternization reaction has been substantially completed.

Subsequently, the substantially saturated fatty acid compound is added to the reaction mixture. Prior to the addition, the remaining quaternizing agent may be removed from the reaction mixture, e.g., by stripping the reaction mixture with nitrogen gas. However, this is not a requirement. After addition of the fatty acid, the mixture is heated to from about 80 to about 150° C. and especially from about 90 to about 130° C. After a period of time, ranging from 1 minute to 10 hours, preferably from 5 minutes to 2 hours, more preferably from 15 minutes to 1.5 hours, the solvent is removed either by distillation, sparging, vacuum stripping, evaporation, or any combination of these processes in any order. Any residue of quaternizing agent and other volatile components present in the reaction mixture will then also be removed.

Sparging is generally conducted by passing an inert gas such as nitrogen or carbon dioxide, or combinations thereof through the mixture.

The solvent may also be removed under reduced pressure of from less than $10^2$ Pa to about $10^5$ Pa, and especially from $10^3$ to $4 \times 10^4$ Pa.

A choice of evaporation units to be used in the present invention is found in Ullman's Encyclopedia of Industrial Chemistry, 5th ed., vol. B3, Evaporation, pages 3–13 and 3–14. A unit having a short residence time is preferably applied. More preferably, a thin film evaporator is used. The reaction mixture may optionally be treated prior to the evaporation in a flash evaporator.

The reactants in combination with the fatty acid may be held at a temperature from about 80 to 150° C. and especially from about 90 to 130° C. during the distillation, sparging, vacuum treatment, evaporation, or combinations thereof.

The process of the present invention includes a solidification step. This may be carried out by simply discharging the reactor and cooling the composition. The solidification step may also include a shaping step, such as, e.g., a flaking, granulation, extrusion, or pastillation step. Examples of apparatus to use in the shaping step are cooling extruders, prilling towers, cooling drums, cooling belts, optionally with a pastillation device. When cooling drums are employed, a single drum with feeding roller at the top or a double drum system is preferred. Flakes are preferably crushed in a sieve granulator. The final step would be then to remove the fines by, e.g., screening or sifting.

The process of the present invention is not limited to the amount of quaternary ester ammonium compound in the compositions prepared. Accordingly, compositions may be prepared comprising 10 to 90 wt % of at least one quaternary ester ammonium compound, 90 to 10 wt % of at least one substantially saturated fatty acid compound, and less than 5.5 wt % impurities, preferably less than 4 wt %, more preferably less than 3 wt %. Preferably, the composition comprises 40 to 90 wt % of a quaternary ester ammonium compound and 60 to 10 wt % of a fatty acid compound.

It has surprisingly been found that with the process of the present invention compositions can be prepared having a high active matter and a low level of impurities. More particularly, in the compositions of the present invention the amount of quaternary ester ammonium compound and substantially saturated fatty acid compound are from more than 50 to 90 wt % and especially from 55 to 80 wt % of quaternary ester ammonium compound and from 50 to 10 wt %, especially from 45 to 20 wt % of fatty acid compound. An amount of at least 20 wt % of substantially saturated fatty acid has the advantage of a particularly non-hygroscopic product. The level of impurities is very low, i.e., below 5.5 wt %, preferably below 4 wt %, more preferably below 3 wt % of the total composition. In the preferred embodiments of the present invention, these impurities include isopropanol, the esters thereof, e.g., with fatty acid, methyl ester, choline chloride, and ester amines, such as N,N-dimethylethanolamine ester.

Quaternary ester ammonium compositions according to the present invention can be used in a variety of applications, specifically in those applications where solidified product forms are required and, more specifically, where caking of solid particles, e.g., as a result of water uptake, needs to be avoided. Independent of the end-use, the described characteristics of these products are of special advantage in handling, transport and storage. Applications can be envisaged in detergent, fabric softener, and personal care formulations, as well as as biocides in disinfectants, sanitizers, and wood preservatives.

The following non-limiting examples are presented to further illustrate the present invention.

EXAMPLES

Estefification of N,N-dimethylethanolamine (DMEA)

A standard glass reactor of 1 l was purged with nitrogen and kept under a nitrogen blanket throughout the reaction. 231.4 g (2.6 moles, 30 mole % excess) of DMEA, 416 g (2 moles) of cocoyl fatty acid, 0.712 g of a 50 wt % aqueous solution of $H_3PO_2$, and 0.208 g of Irganox 1076 (benzenepropanoic acid, 3,5-bis(1,1-dimethylethyl)-4-hydroxy-octadecyl ester, ex Akzo Nobel), were charged to the reactor. The reaction mixture was heated up to 130° C. in 30 minutes. Then the temperature is raised in 12 hours from 130 to 200° C. The fatty acid content of the reaction mixture was measured to be below 3 wt %. The reaction mixture was cooled down to 180° C. The excess DMEA was removed by applying a vacuum of $2 \times 10^3$ Pa at 180° C. The reaction mixture was cooled down to room temperature and the reactor was discharged. Yield: 552 g of product comprising 95 wt % cocoyl ester of N,N-dimethylethanolamine.

Comparative Example A

Quaternization in fatty acid

A glass autoclave of 1 l was purged with nitrogen and kept under a nitrogen blanket throughout the reaction. 290 g (1 mole) of cocoyl ester of N,N-dimethylethanolamine and 173 g of lauric fatty acid were charged to the autoclave. The reaction mixture was heated up to 90° C. in 30 minutes. Then the addition of methyl chloride in gas form was started. The reaction pressure was kept below $4 \times 10^5$ Pa. The reaction mixture was heated up to 100° C. When a total of 56 g (1.1 moles) of methyl chloride was charged the addition was stopped. The reaction was continued until the free amine level was below 3 wt %. Then, the reactor was depressurized and stripped with nitrogen gas for 5 hours to remove excess methyl chloride. The reaction mixture was cooled down to 85° C. and the reactor was discharged. Yield 513 g of product A. Analyses of product A are listed in Table 1.

Example 1

Quaternization in Isopropanol

A glass autoclave of 1.5 l was purged with nitrogen and kept under a nitrogen blanket throughout the reaction. 580 g (2 moles) of cocoyl ester of N,N-dimethylethanolamine and 165 g of isopropanol were charged to the autoclave. The reaction mixture was heated up to 50° C. in 30 minutes. Then the addition of methyl chloride in gas form was started. The reaction pressure was kept below $3 \times 10^5$ Pa. Due to the heat of reaction the reaction temperature increased to 85° C. and was stabilized at 70° C. by cooling the reaction mixture. When a total of 111 g (2.2 moles) of methyl chloride was charged the addition was stopped. The reaction was continued until the free amine level was below 2 wt %. The reaction mixture contained during the reaction less than 0.2 wt % water. Then, the reactor was depressurized and stripped with nitrogen gas for 5 hours to remove excess methyl chloride. The reaction mixture was cooled down to 50° C. and discharged.

A reactor of 2 l was purged with nitrogen and kept under a nitrogen blanket throughout the reaction. The above-mentioned reaction mixture was charged to the reactor. .475 g of cocoyl fatty acid was added to the reaction mixture. The reaction mixture was heated up to 120° C. and maintained for 1 hour. The pressure was decreased slowly to $2 \times 10^3$ Pa in 1 hour and then kept at 30 minutes at $2 \times 10^3$ Pa to remove isopropanol and remaining methyl chloride. The reactor was discharged at 110° C. Yield 1154 g of product 1. Analyses of product 1 are listed in Table 1.

TABLE 1

|  | A<br>dod | 1<br>coc |
|---|---|---|
| CEQ[1] | 52.9 | 56.5 |
| fatty acid | 40.6 | 40.6 |
| choline chloride | 0.2 | 0.2 |
| ester amine | 3.3 | 1.3 |
| methyl ester | 3.0 | 1.2 |
| isopropanol ester | — | 0.3 |
| isopropanol | — | — |
| total of impurities | 6.5 | 3.0 |

All numbers are percentages by weight
dod = dodecyl (lauric) fatty acid (Kortacid 1299, IV = 0.2)
coc = cocoyl fatty acid (Kortacid 1270, IV = 1), a mixture of 70% dodecyl and 30% tetradecyl fatty acid
IV = Iodine Value, expressed in g iodine per 100 g fatty acid
[1]CEQ = cocdyl ester of (2-hydroxyethyl)trimethylammonium chloride As can be seen from the compositions listed in Table 1, the process of the present invention results in a composition with far less impurities than the process of the prior art.

Examples 2–8 and Comparative Example B

Example 1 was repeated by adding several fatty acid compounds in different amounts in the reaction mixture. Also Comparative Example A was repeated by replacing lauric acid with hardened tallow fatty acid in a higher amount. The results are listed in Table 2.

TABLE 2

|  | B<br>HT[1] | 2<br>HT | 3<br>dod | 4<br>tet | 5<br>coc | 6<br>hex | 7<br>oct | 8<br>coc |
|---|---|---|---|---|---|---|---|---|
| CEQ[2] | 47.7 | 48.8 | 50.8 | 50.0 | 50.2 | 50.2 | 49.6 | 60.3 |
| fatty acid | 45.4 | 48.7 | 47.4 | 48.0 | 47.9 | 47.7 | 48.2 | 36.4 |
| cc[3] | — | 0.1 | 0.1 | 0.1 | 0.1 | 0.1 | 0.1 | 0.1 |
| ester amine | 2.9 | 0.8 | 0.7 | 0.7 | 0.7 | 0.7 | 0.8 | 1.9 |
| methyl ester | 3.9 | 1.2 | 0.9 | 1.1 | 0.9 | 1.1 | 1.3 | 1.3 |
| ipa[4] ester | — | 0.3 | 0.1 | — | 0.1 | 0.1 | — | — |
| ipa | — | — | 0.1 | 0.1 | 0.1 | — | — | — |
| total imp. | 6.8 | 2.4 | 1.9 | 2.0 | 1.9 | 2.0 | 2.2 | 3.3 |

All numbers are percentages by weight
[1]HT = hardened tallow fatty acid (Edenor FHTi, IV = 1)
dod = dodecyl (lauric) fatty acid (Kortacid 1299, IV = 0.2)
tet = tetradecyl (myristic) fatty acid (Kortacid 1499, IV = 0.2)
coc = cocoyl fatty acid (Kortacid 1270, IV = 1), a mixture of 70% dodecyl and 30% tetradecyl fatty acid
hex = hexadecyl (palmitic) fatty acid (Kortacid 1698, IV = 1)
oct = octadecyl (stearic) fatty acid (Kortacid 1895, IV = 2)
IV = Iodine Value, expressed in g iodine per 100 g fatty acid
[2]CEQ = cocoyl ester of (2-hydroxyethyl)trimethylammonium chloride
[3]cc = choline chloride
[4]ipa = isopropanol Comparing the results of Examples 2–8 with the results of Comparative Example B, it can be seen that the total amount of impurities in the compositions prepared according to the process of the prior art is higher than the amount of impurities in the compositions prepared according to the process of the present invention.

Example 9 and Comparative Example C

Pilot Plant Scale

Comparative Example C

Quaternization in Fatty Acid

A glass-lined autoclave of 100 l was purged with nitrogen and kept under a nitrogen blanket throughout the reaction. 32 kg (110 moles) of cocoyl ester of N,N-dimethylethanolamine and 24 kg of cocoyl fatty acid were charged to the autoclave. The reaction mixture was heated up to 70° C. in 40 minutes. Then the addition of methyl chloride in gas form was started. The reaction pressure was kept below $4 \times 10^5$ Pa. Due to the heat of the reaction the reaction temperature was increased to 95° C. and was stabilized at 85° C. by cooling the reaction mixture. When a total of 6.5 kg (129 moles) of methyl chloride was charged the addition was stopped. The reaction was continued until the free amine level was below 4 wt %. Then, the reactor was depressurized and stripped with nitrogen gas for 3 hours to remove excess methyl chloride. The reaction mixture was cooled down to 85° C. and the reactor was discharged. Yield 61 kg of product C. Analyses of product C. are listed in Table 3.

Example 9

Quaternization in Isopropanol

A glass-lined autoclave of 100 l was purged with nitrogen and kept under a nitrogen blanket throughout the reaction. 41.1 kg (142 moles) of cocoyl ester of N,N-dimethylethanolamine and 16.7 kg of isopropanol were charged to the autoclave. The reaction mixture was heated up to 55° C. in 30 minutes. Then the addition of methyl chloride in gas form was started. The reaction pressure was kept below 3×10⁵ Pa. Due to the heat of reaction the reaction temperature increased to 75° C. and was stabilized at 70 to 75° C. by cooling the reaction mixture. When a total of 8.4 kg (166 moles) of methyl chloride was charged the addition was stopped. The reaction was continued until the free amine level was below 2 wt %. The reaction mixture contained less than 0.2 wt % of water during the reaction. Then, the reactor was depressurized and stripped with nitrogen gas for 3 hours to remove excess methyl chloride. 38 kg of cocoyl fatty acid were charged to the reaction mixture. The reaction mixture was heated up to 115° C. and maintained for 1 hour. The pressure was decreased slowly to 15×10³ Pa in 1 hour and then kept at 115° C. and 15×10³ Pa for 5 hours to remove isopropanol and remaining methyl chloride. The reactor was discharged at 110° C. Yield 86 kg of product 9. Analyses of product 9 are listed in Table 3.

TABLE 3

|  | C coc | 9 coc |
|---|---|---|
| CEQ[1] | 54.8 | 50.1 |
| fatty acid | 38.6 | 46.5 |
| choline chloride | 0.4 | 0.6 |
| ester amine | 3.7 | 1.0 |
| methyl ester | 2.4 | 0.9 |
| isopropanol ester | — | 0.9 |
| isopropanol | — | 0.1 |
| total of impurities | 6.5 | 3.5 |

All numbers are percentages by weight
coc = cocoyl fatty acid (Kortacid 1270, IV = 1), a mixture of 70% dodecyl and 30% tetradecyl fatty acid
IV = Iodine Value, expressed in g iodine per 100 g fatty acid
[1]CEQ = cocoyl ester of (2-hydroxyethyl)trimethylammonium chloride Properties tests on the products of Examples 3, 4, 6, 10,11, and 12
Granules Granules were prepared at bench scale. 500 ml of the compositions described in Table 4 were poured as liquids on trays of size 0.6×1.0 m. Using a spatula knife an even thin layer was made and the liquid was allowed to solidify. The flakes were removed and crushed in a sieve granulator with 1.25 aperture. The fines from the crushed product were removed using a 280 μm screen.

Caking Upon Storage

This test reflects the behavior of granules stored in big bags. 30 g of a sample as prepared above was filled in a caking test cylinder and placed under a load of steel balls simulating the weight of about 1 meter product column, corresponding with the size of a big bag. The cylinder was stored for 24 h at 40° C. The cylinder was subsequently carefully unloaded. The sample was placed on a vibrating screen with an amplitude of 1 mm for max. 120 seconds. The time to obtain an empty screen was observed. Also the weight of residue left behind on the screen after 120 seconds was determined.

Dissolution

The dissolving time is expressed by the neutralization rate of a dispersion of 200 mg of composition in 150 ml of water at 40 ° C. and a pH of 9.5, in which process the insoluble fatty acid was converted into its soluble neutralized salt. The neutralization process was followed by measuring the amount of an 0.1N NaOH solution to be added to maintain a constant pH value of 9.5 with a Metrohm 632 pH measuring device. The dissolving time is defined as the time required for the neutralization of half of the composition used.

Hygroscopicity

A sample of about 5 g of composition was weighted accurately. The sample was put evenly into a 10 cm diameter disc. The disc was stored overnight on a table. Moisture of the air was recorded to be RH=50–60%. The weight increase was noted.

Examples 3, 4, and 6 (see Table 2) were tested on the above-mentioned properties. Examples 10, 1 1, and 12 corresponding to Examples 3, 4, and 6, respectively, but all containing 35 wt % fatty acid, were also tested. In Example D, partially hydrogenated tallow fatty acid was used. The results are listed in Table 4.

TABLE 4

|  | C coc | D pHT | 3 dod | 4 tet | 6 hex | 10 dod | 11 tet | 12 hex | 13 |
|---|---|---|---|---|---|---|---|---|---|
| caking value (sec) | >120 | >120 | >120 | 100 | 95 | 15 | 12 | 13 | nd |
| residue (%) | 100 | 90 | 10 | 0 | 0 | 0 | 0 | 0 | nd |
| dissolving time (sec) | nd | nd | 310 | 210 | 84 | 48 | 42 | 66 | 160 |
| hygroscopicity (%) | 1 | nd | 0 | 0 | 0 | 0 | 0 | 0 | 0 | nd = not determined
coc = cocoyl fatty acid (Kortacid 1270, IV = 1), a mixture of 70% dodecyl and 30% tetradecyl fatty acid
pHT = partially hydrogenated tallow fatty acid (Radiacid 448, IV = 20)
dod = dodecyl (lauric) fatty acid (Kortacid 1299, IV = 0.2)
tet = tetradecyl (myristic) fatty acid (Kortacid 1499, IV = 0.2)
hex = hexadecyl (palmitic) fatty acid (Kortacid 1698, IV = 1)
IV = Iodine Value, expressed in g iodine per 100 g fatty acid As can be seen from the results in Table 4 the Examples show that compositions according to the invention comprising a substantially saturated fatty acid are much more resistant against caking upon storage and have much less or no residue than a composition comprising an unsaturated fatty acid.

Example 13

In a 1 I three-necked round bottom flask provided with a temperature controlling unit and a 30 cm column was added 130 g (1.1 moles) of 3-dimethylamino-1,2-propanediol (ex Aldrich) and 544 g (20 moles) of molten hydrogenated tallow acid (Interstab G 8207). The homogeneous mixture was stirred for 4 h at 190° C. and 10⁴ Pa to remove reaction water completely. GC analysis showed 90.4% diester amine, 4.9% monoester amine, and 4.7% free fatty acid.

A glass autoclave of 1.5 l, purged with nitrogen, was filled with the esterification product (theoretically 638 9 of diester) and 120 g of acetone was added. The reactor content was heated to 95° C. Gaseous methyl chloride was added in portions until the quaternization was complete after 7 h. The reactor was depressurized and cooled to 80° C. Hardened tallow fatty acid (342 g, Edenor FHTi, IV=1) was added to this reaction mixture. The mixture was heated to 105° C. and maintained at this temperature for 1 h. The pressure was slowly decreased to 2×10³ Pa to remove low boiling compounds. The liquid product was poured as a thin layer onto trays of 40×60 cm. The liquid solidified and hardened in minutes. The solid product was collected as crispy flakes. The properties of this product are depicted in Table 4.

We claim:

1. A process for preparing a solid composition comprising at least one quaternary ester ammonium compound and at least one fatty acid compound which comprises:

quaternizing a tertiary ester amine with a quaternizing agent in a substantially water-free solvent in the absence of a fatty acid to obtain a quaternary ester ammonium compound, adding a substantially saturated fatty acid to the reaction mixture comprising the quaternary ester ammonium compound, and solidifying the resulting mixture.

2. The process of claim 1, wherein the quaternary ester ammonium compound is formulae I or II:

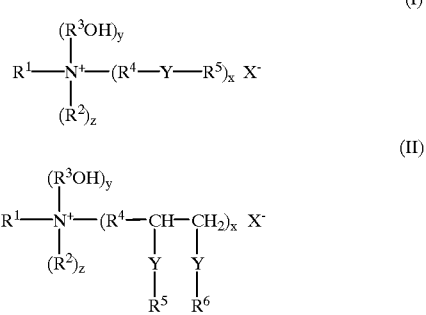

wherein

X⁻ is an anion;

Y is —O—C(O)—, —C(O)—O—, or —O—C(O)—O—;

x, y, and z are independently chosen from a range from 0 to 3, whereby x+y+z=3, and x is not 0;

R¹ is a linear or branched $C_{1-30}$ alkyl group, optionally comprising one or more unsaturated bonds;

R² is a linear or branched $C_{1-4}$ alkyl group, optionally substituted with one or more hydroxyl groups or a phenyl group;

R¹ and R² may be linked together to form a ring with the central quaternary nitrogen atom, optionally via a heteroatom selected from the group consisting of nitrogen, oxygen, and sulfur;

R³ is a linear or branched $C_{1-30}$ alkylene group, optionally comprising one or more unsaturated bonds;

R⁴ is a linear or branched $C_{1-4}$ alkylene group, optionally comprising one or more unsaturated bonds, optionally substituted with one or more hydroxyl groups; and R⁵ and R⁶ are independently a linear or branched $C_{1-30}$ alkyl group, optionally comprising one or more unsaturated bonds, ester, or ether groups.

3. The process of claim 2, wherein the quaternary ester ammonium compound is formula I.

4. The process of claim 3, wherein R¹ and R² are methyl groups and x=1, y=0, and z=2.

5. The process of claim 3, wherein R¹ is a methyl group and x=1, y=2, and z=0.

6. The process of claim 3, wherein R¹ and R² are methyl groups and x=1, y=1, and z=1.

7. The process of claim 2, wherein X⁻ is selected from the group consisting of chloride, bromide, iodide, fluoride, sulfate, methyl sulfate, nitrate, formate, phosphate, dimethyl phosphonate, carbonate, borate, acetate, propionate, citrate, adipate, and benzoate.

8. The process of claim 2, wherein Y is —O—C(O)—.

9. The process of claim 2, wherein R⁴ is an ethylene group.

10. The process of claim 2, wherein R⁵ and/or R⁶ are selected from the group consisting of $C_{6-30}$ alkyl groups, heptyl, nonyl, undecyl, tridecyl, pentadecyl, heptadecyl, heptadecenyl, heptadecadienyl, nonadecyl, and henicosyl groups, and mixtures thereof.

11. The process of claim 10, wherein R⁵ and/or R⁶ are selected from the group consisting of heptyl, nonyl, undecyl, and tridecyl groups, and mixtures thereof.

12. The process of claim 1, wherein the solvent is a polar volatile solvent.

13. The process of claim 12, wherein the solvent is selected from the group consisting of $C_{1-5}$ alkanols, methanol, ethanol, propanol, butanol, pentanol, isomers of $C_{1-5}$ alkanols, isopropanol, isobutanol, t-butanol and combinations thereof.

14. The process of claim 13, wherein the solvent is isopropanol.

15. The process of claim 1, wherein the substantially saturated fatty acid has an iodine value of from 0 to less than 3.

16. The process of claim 15, wherein the iodine value of said substantially saturated fatty acid is from 0 to 1.

17. The process of claim 1, wherein the substantially saturated fatty acid is a linear or branched $C_{12-22}$ fatty acid.

18. The process of claim 17, wherein the fatty acid is lauric, myristic, palmitic, stearic, or cocoyl fatty acid.

19. The process of claim 1, wherein the solidification step includes a shaping step of flaking, granulation, extrusion or pastillation.

* * * * *